(12) United States Patent
Bader et al.

(10) Patent No.: US 8,496,773 B2
(45) Date of Patent: Jul. 30, 2013

(54) DIAPER CLOSURE AND METHOD OF MAKING SAME

(75) Inventors: Herbert Bader, Nordwalde (DE);
Marcus Schoenbeck, Versmold (DE);
Mike Rolefs, Steinfurt (DE); Andreas Hagemann, Gronau (DE); Olga Fezert, Lingen (DE)

(73) Assignee: Mondi Consumer Packaging Technologies GmbH, Gronau (DE)

( * ) Notice: Subject to any disclaimer, the term of this patent is extended or adjusted under 35 U.S.C. 154(b) by 115 days.

(21) Appl. No.: 12/871,501

(22) Filed: Aug. 30, 2010

(65) Prior Publication Data

US 2012/0037300 A1      Feb. 16, 2012

(30) Foreign Application Priority Data

Sep. 28, 2009   (EP) ..................................... 09012277

(51) Int. Cl.
   *B32B 3/02*       (2006.01)
(52) U.S. Cl.
   USPC .......... 156/160; 156/196; 156/66; 156/306.6; 156/220; 156/253; 156/229; 428/192; 442/328; 604/389; 604/385.04
(58) Field of Classification Search
   USPC ................... 156/66, 306.6, 220, 60, 253, 229, 156/160; 428/192; 442/328; 604/389, 385.04
   See application file for complete search history.

(56) References Cited

U.S. PATENT DOCUMENTS

| | | | |
|---|---|---|---|
| 5,900,101 A | 5/1999 | Justmann | |
| 6,195,850 B1 | 3/2001 | Melbye | |
| 6,255,236 B1 | 7/2001 | Cree | |
| 6,780,272 B2 | 8/2004 | Wood | |
| 6,875,710 B2 | 4/2005 | Eaton | |
| RE39,307 E * | 9/2006 | Zhou | 525/191 |
| 2008/0070007 A1* | 3/2008 | Vincent et al. | 428/192 |

FOREIGN PATENT DOCUMENTS

DE         102004035649 B       3/2006

* cited by examiner

*Primary Examiner* — Jeff Aftergut
*Assistant Examiner* — Jaeyun Lee
(74) *Attorney, Agent, or Firm* — Andrew Wilford (57) ABSTRACT

A laminated web from which diaper closure elements may be punched is made by first applying at least two pairs longitudinally extending and transversely spaced bend-resistant strips to a first longitudinally extending nonwoven tape. Then a respective longitudinally extending strip of an elastically stretchable polymer is applied to the first nonwoven tape between each of the pairs of the bend-resistant strips with the polymer strip partially overlapping both of the bend-resistant strips of the respective pair. A second longitudinally extending nonwoven tape that covers and extends transversely to both sides of the polymer strip is applied over the bend-resistant strips and the polymer strips to form a laminate with the polymer strip between the first and second nonwoven tapes.

15 Claims, 13 Drawing Sheets

DIAPER CLOSURE AND METHOD OF MAKING SAME

FIELD OF THE INVENTION

The present invention relates to a closure. More particularly this invention concerns a method of making a side closure for use on a disposable diaper.

BACKGROUND OF THE INVENTION

A web from which may be punched diaper closure elements has an elastically stretchable region and inelastic connecting regions for attaching to a diaper as well as for connecting a closure part. With the method on which the invention is based, parallel and spaced-apart film strips of an elastically extensible polymer are laminated between two tapes of nonwoven material.

DE 10 2004 035 649 relates to a method with the above-described characteristics for making diaper closure elements. Between the elastic film strips the nonwoven tapes are glued directly to each other. The diaper closure elements punched from the web each have an elastically stretchable region and adjoining connecting regions on both ends of the nonwoven material. The diaper closure elements may be formed as short straps or may be in the form of so-called diaper ears whose connecting regions to a diaper are longer than the connecting region for fastening the closure part. Large forces are transmitted to the diaper closure elements via the closure part. For uniform introduction of forces into the diaper closure element it is advantageous to have a bending-resistant connecting region of high tensile strength. Furthermore it must be ensured that the connecting regions made of nonwoven material do not become frayed or permanently stretched if during use the diaper closure elements are stretched up to the elongation limit of the elastic region.

EP 1,252,015 describes a diaper closure element where the core layer is an elastic film that has nonwoven layers laminated to both its faces. The nonwoven layers and the core layer have the same external dimensions, i.e. the elastic core layer is as long in its stretch direction as the nonwoven layers laminated onto it on both faces. Both the connecting region for the closure part and the connecting region for fastening to a diaper are stiffened by a layer of inelastic polymer. Stiffening is accomplished by a tension-resistant film of for example polypropylene homopolymer that is laminated between the elastic film and one of the two outer layers in the connecting regions and that counteracts the elasticity of the elastic core layer. Since elastic polymers are expensive, there is a need for keeping the elastic polymer content in the bond as low as possible without disadvantageously affecting the elasticity and the mechanical properties of the bonding material.

U.S. Pat. No. 6,255,236 discloses a diaper closure element comprising a support with elastic and inelastic regions. The support, in particular, consists of a coextruded film with an elastic core layer and inelastic outer layers. A textile web is laminated onto one face of the support. The other face of the support has a closure part attached to it. Due to localized stretching that causes the inelastic outer layers of the support and the laminated-on nonwoven material to be overstretched in some regions, an elastically stretchable region is created. This is called selective mechanical activation. Here also it is disadvantageous that the elastic support extends over the whole length of the diaper closure element including the inelastic connecting regions. Another disadvantage is that the diaper closure element has a textile surface on one face only.

U.S. Pat. No. 6,875,710 describes a diaper closure element comprising a textile support consisting for example of nonwoven material. In specified regions the support is reinforced by a strip or layer of inelastic polymer applied in a thermoplastic state and at least partially permeating the fibrous structure of the nonwoven layer. In another region spaced therefrom, the support has a coating consisting of a thermoplastic elastomer that at least partially also permeates the fibrous structure of the nonwoven material forming an elastically stretchable region. The inelastic and elastic regions are spaced from one another. Due to the spacing, the transmission of forces between the reinforced or stiffened inelastic regions and the elastic region is unsatisfactory. If the material is stretched up to the elongation limit of the elastic region, there is a risk that the material between the elastic region and the inelastic regions consisting exclusively of nonwoven material is permanently deformed and destroyed.

OBJECTS OF THE INVENTION

It is therefore an object of the present invention to provide an improved method of making a diaper closure element.

Another object is the provision of such an improved method of making a diaper closure element that overcomes the above-given disadvantages, in particular that produces closure elements that have a bending-resistant and tension-proof connecting region for a closure part.

SUMMARY OF THE INVENTION

A web from which diaper closure elements may be punched is made by a method where first at least two pairs of longitudinally extending and transversely spaced bend- and/or stretch-resistant reinforcement strips are applied to a first longitudinally extending nonwoven tape. Then a respective longitudinally extending strip of an elastically stretchable polymer is applied to the first nonwoven tape between each of the pairs of the bend-resistant strips with the polymer strip partially overlapping both of the bend-resistant strips of the respective pair. A second longitudinally extending nonwoven tape that covers and extends transversely to both sides of the polymer strip is applied over the bend-resistant strips and the polymer strips to form a laminated web with the polymer strip between the first and second nonwoven tapes. The desired diaper closure elements are then punched with one end of each element lying between the bend-resistant strips between one of the pairs of bend-resistant strips and an opposite end of each element lying between the respective pair of bend-resistant strips and adjacent pair of bend resistant strips.

Preferably the laminate according to the invention has a sequence of three longitudinally extending and transversely spaced zones repeating several times on the longitudinally traveling tapes. In each first zone the nonwoven tapes are directly connected with each other. A second zone is elastically extensible and has outer layers of nonwoven material as well as an elastic film strip as an intermediate or core layer. The third zone has two outer layers of nonwoven material and a reinforcing layer as intermediate layer. For the method according to the invention it is essential that the layer of elastic film strips and the reinforcing layers are positioned relative to each other such that the reinforcing layers each fill the gaps between two elastic film strips and actually transversely overlap the adjoining elastic film strips in the regions on both edges. Conveniently the overlapping regions have a width of between 2 mm and 10 mm. This ensures uniform transmission of forces between the elastically stretchable region and the adjoining sections, if during use of the diaper closure elements manufactured according the method of the invention tensile forces are applied to the connecting region reinforced by a bend-resistant reinforcing strip.

According to the method of the invention diaper closure elements may also be manufactured that comprise a reinforced connecting region for connecting a closure part and a soft flexible connecting region for attaching to a diaper. Here only the connecting region for connecting a closure part is reinforced with a reinforcing layer serving to stiffen it, whereas the other connecting region for attaching to the diaper consists only of the two nonwoven layers directly laminated to each other and forming a soft flexible connecting region that can adapt well to the shape of a diaper. Attaching the reinforcing layers to a first nonwoven tape may be done in various ways. A first embodiment of the method according to the invention provides for the reinforcing layers to be applied to the first nonwoven tape by extrusion coating, an additional perforated film preferably being provided between the inelastic polymer for the reinforcing layers and the nonwoven tape for the following reasons.

The reinforcing layers between the nonwoven tapes have both a high bending resistance and a high resistance to tear propagation. These two requirements cannot be simultaneously met to the desired extent merely by polymer selection. If a brittle polymer is selected good bending resistance values will result. However the resistance to tear propagation diminishes as the brittleness of the polymer decreases. The nonwoven material that has a high resistance to tear propagation takes over the bad tear propagation properties of the polymer if the polymer is applied all-over, that is with the full-surface coverage. If an elastic polymer is used, the resistance to tear propagation is improved, but to the detriment of a diminishing bending resistance. If, however, a perforated film is arranged as an intermediate layer between the first nonwoven tape and the reinforcing layers applied by extrusion coating, brittle polymers may be used for producing reinforcing layers without this having a disadvantageous effect on the resistance-to-tear propagation of the laminate. The polymer that is extrusion-coated in a molten state is forced through the holes in the perforated film into the nonwoven material so that the polymer is no longer bonded full-surface but only selectively to the nonwoven material, that is in partial-surface coverage. The polymer compound of the reinforcing layer is thus decoupled from the nonwoven material so that the good tear propagation properties of the nonwoven material come into play. According to a preferred embodiment of the method according to the invention a perforated film is laid on the first nonwoven tape at least in the region of the reinforcement layers to be applied, and the inelastic polymer for the reinforcement is then applied to the perforated film by an extrusion coating process so that the molten polymer penetrates through the perforations in the film and is forced into the nonwoven tape at the perforations. Attachment of the perforated film preferably takes place only as a result of the molten polymer penetrating through the perforations in the course of the extrusion process. The perforated films may be made of low-cost polymers, since the function described is determined, in the first place, by the number and size of the perforations and since the mechanical properties of the perforated film are of lesser importance. It is, however, important that the polarity of the perforated film matches that of the polymer used for the extrusion coating.

Application of the polymer is preferably done using a tool that engages the web to be coated, thereby ensuring that the polymer for the reinforcing layer is forced into and penetrates the structure of the web, i.e. into the structure of the nonwoven material and if necessary through the perforations in the laminated-on perforated film.

The strip-like polymer application may be performed locally in a uniform coating thickness or as a pattern composed of polymer-filled regions and polymer-free regions. Extrusion coating may be done using a roller whose surface may have a profiled structure consisting of elevations and/or depressions. Due to the profiled roller surface a polymer pattern with different application amounts is produced, and the stiffening effect may be influenced. Moreover the structure of elevations and/or depressions causes the polymer to penetrate further into the nonwoven material of the web to be coated. With the use of a structured roller a sufficiently secure bond can also be achieved using a curtain coating method, in which the molten polymer is firstly laid onto the web that is to be coated.

Alternatively the application tool for the extrusion coating may be a coating nozzle with a plurality of apertures spaced from one another according to the spacing of the reinforcing layers. Or coating nozzles arranged in a parallel array may be used as application tools with a spacing that is preferably adjustable. The application of the polymer in the region of the reinforcing layers is done locally or in a pattern. The method according to the invention is not limited to producing the reinforcing layers by way of extrusion coating. It also lies within the scope of the invention to manufacture the reinforcing strips from a bend-resistant polymer film or from a nonwoven material. Bonding the reinforcing strips to the nonwoven tape is done thermally or by gluing.

One embodiment of the method according to the invention provides for heating the reinforcing strips and pressing them into the nonwoven tape while still hot. In particular, the reinforcing strips can be bonded to the nonwoven tape by embossing rollers using pressure and heat. Here a thermal bond can also be achieved using ultrasound welding. It is also within the scope of the invention that a thermal bond is only created if the reinforcement strips are arranged between the first and the second nonwoven tape, the bond then being with both nonwoven tapes. Further the reinforcing strips can be glued to the nonwoven tapes on both faces. Gluing is preferably done such that the glue bonds on both faces of the reinforcing strips are of different adhesive strength. Weak adhesive strength between reinforcing strips and the adjoining nonwoven tape on at least one face of the laminate has an advantageous effect on the resistance-to-tear propagation of the bond.

Different adhesive strengths on both faces of a reinforcing layer may be achieved by bonding the reinforcing strips to the respective adjoining nonwoven tape, using a full-surface application of adhesive on one face and a partial application of adhesive on the other face. For the partial application of adhesive a swirl nozzle technique may be used, in particular. To improve the adherence of the adhesive, the reinforcing strips may be pretreated on one face or on both faces. Pretreatment of the reinforcing strips on one face only may also be utilized in order to selectively achieve different levels of adhesion of the adhesive on both faces of the reinforcing layer.

Independently of whether the reinforcing layers are produced from laminated-in bend-resistant polymer films or by extrusion coating, the reinforcing layers may be produced, in particular, from polyolefins, polyolefin copolymers, styrene polymers, cycloolefin copolymers, polyamides, a polyactide, polyester, thermoplastic polyurethanes or mixtures of these polymers. The bond between the nonwoven tapes and the laminated-in elastic film strips is preferably achieved by a hot-melt adhesive. After the laminating process the web further conveniently passes through a set of rollers consisting of meshing profiled stretching rollers in which the web is stretched transversely to the moving direction of the web in the region of the laminated-in elastic film strips. Stretching causes the elastic regions of the web to be activated so that the diaper closure elements punched out of it can be stretched up to a distinctly noticeable stretching limit using only a small amount of force.

BRIEF DESCRIPTION OF THE DRAWING

The above and other objects, features, and advantages will become more readily apparent from the following description, reference being made to the accompanying drawing in which:

FIG. 5A to 5H show various patterns of the polymer application forming a reinforcing layer during execution of the method illustrated in FIG. 2;

SPECIFIC DESCRIPTION

Figure 1:
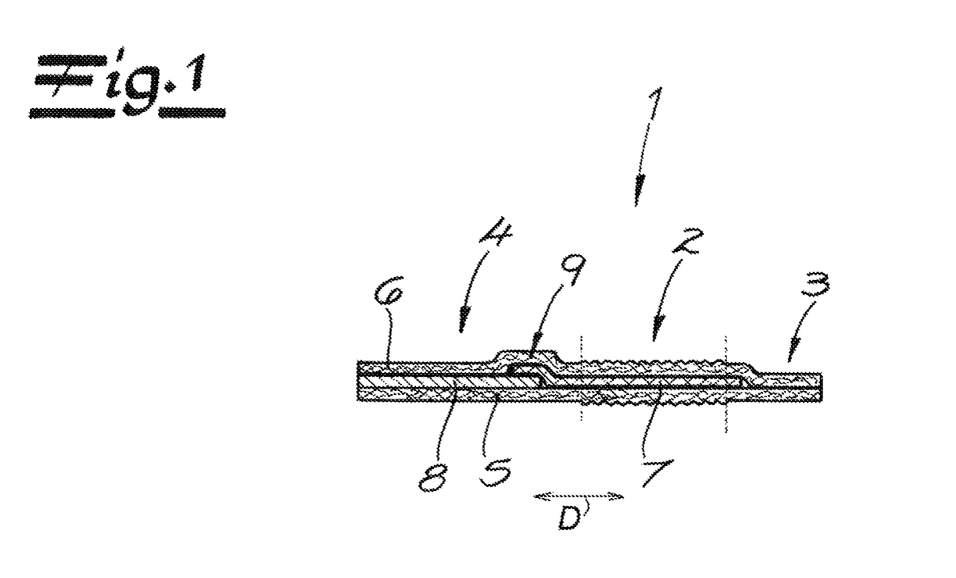
FIG. 1 is a longitudinal section through a diaper closure element manufactured according to the method of the invention in its stretch direction.

The diaper closure element 1 shown in FIG. 1 has an elastically stretchable region 2, an inelastic connecting region 3 for attaching to an edge of a diaper as well as a further inelastic connecting region 4 for attaching to a closure part. The diaper closure element 1 is a laminate and has outer layers 5 and 6 of nonwoven material as well as an elastic film layer 7 laminated between the outer layers 5 and 6. The outer layers 5 and 6 are longer in a stretch direction D than the elastic film layer 7 and are bonded together to each side of the elastic layer 7 in overhanging sections that form the inelastic connecting regions 3 and 4. The connecting region 3 for fastening to a diaper is soft and flexible and is composed of only the two nonwoven layers 5 and 6 bonded directly together with each other. The connecting region 4 for the closure part, on the other hand, is stiffened by a reinforcing layer 8 that in a region 9 overlaps the layer 7 between the outer layers 5 and 6. The overlapping region 9 is approximately 2 mm to 10 mm long. The reinforcing layer 8 consists of a polymer that, in comparison to the mechanical properties of the elastic film layer 7, is characterized by a substantially higher bending resistance and higher tensile strength. Suitable polymers are polyethylene, polypropylene, in particular polypropylene homopolymers, polyolefin copolymers, styrene polymers, cycloolefin copolymers, polyamides, polyactide, thermoplastic polyurethanes or mixtures of these polymers.

The elastically stretchable region 2 has been activated by monoaxial stretching of the portion of the laminate containing the laminated-in elastic layer 7. This locally limited stretching overstretches the fibers of the nonwoven layers 5 and 6 in this region, thereby reducing its stretch resistance. The stretched region is shorter than the elastic film layer 7 and ends before the overlapping region 9.

Figure 2:
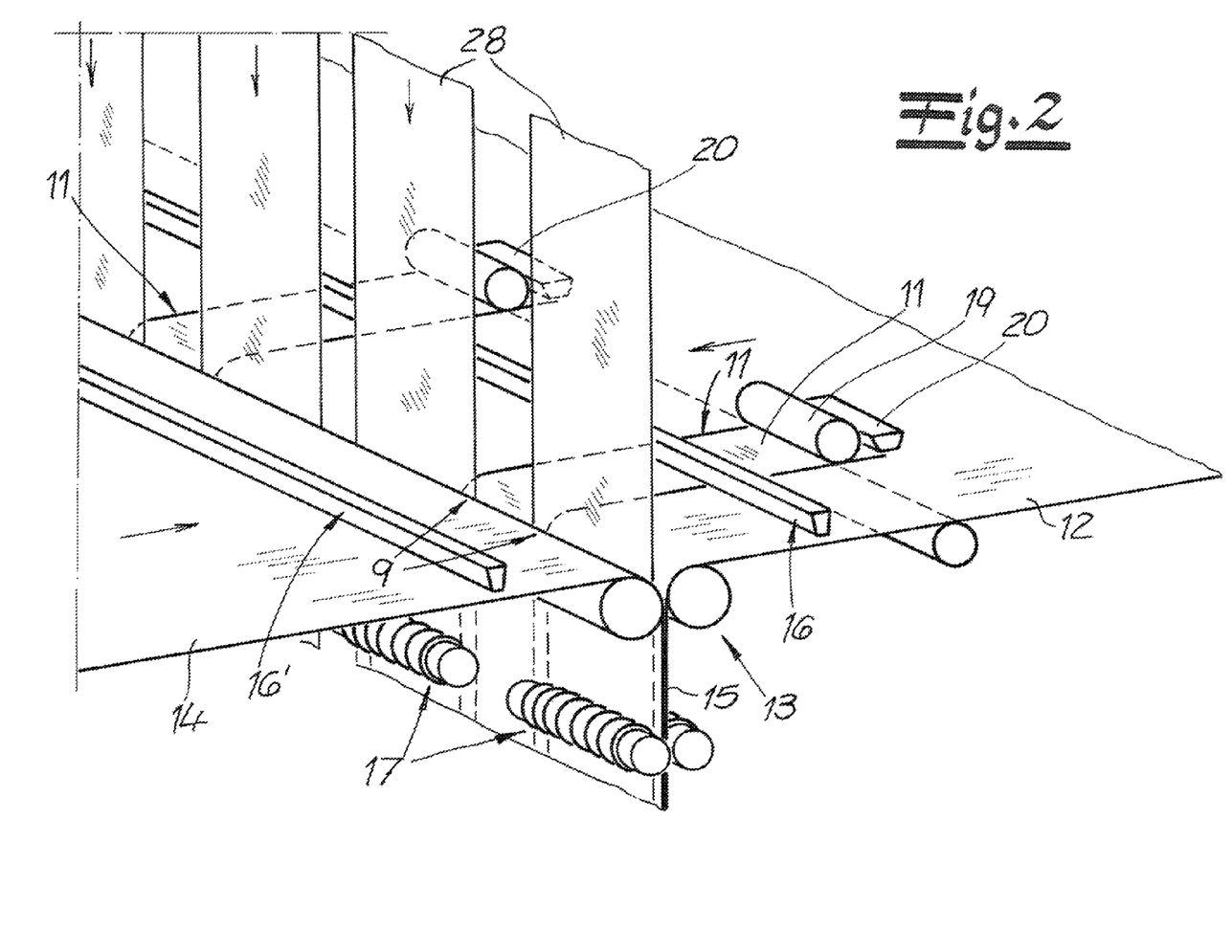
FIG. 2 is a perspective view showing a method of making a web from which diaper closure elements according to FIG. 1 may be punched.

FIG. 2 shows a process for making a laminated web 15 from which the FIG. 1 diaper closure elements 1 may be punched. First, parallel and spaced strips 11 of an inelastic polymer that will form the bend-resistant reinforcing layers 8 are applied to one face of a first nonwoven tape 12 that will form the layer 5. Then the first nonwoven tape 12 is bonded in a laminating apparatus 13 to elastic film strips 26 that will form the elastic layer 7 and to a second nonwoven tape 14 that will form the layer 6, to form the multilayer laminated web 15. The tapes 12 and 14 and the strips 11 and 28 of the laminate are glued together by application of an adhesive, according to the illustration in FIG. 2 for example, at stations 16 and 16' to the inside faces of the nonwoven tapes 12 and 14. Application of the adhesive is done locally or in a regular pattern consisting of adhesive-free regions and adhesive regions. Conveniently hot-melt adhesives are used. The elastic strips 28 and the reinforcing layers strips 11 are positioned relative to each other in such a way during execution of the method that the strips 11 fill the gap between two elastic film strips 7 and are glued to the adjoining elastic film strips 7 to form the overlapping regions 9 on both edges.

Following the laminating process, each region corresponding to one of the elastic strips 28 of the laminated web 15 passes between a set of meshing profiled rollers 17 that transversely stretch the web 15 at each strip 11, that crosswise to the travel direction of the web 15. Each roller 17 has a plurality of annular ridges that interleave with the ridges of the other roller so that the laminate 15 is transversely stretched. Thus causes the stretchable regions to be activated, so that stretch resistance is reduced in the stretchable regions of the web 15.

Figure 3:
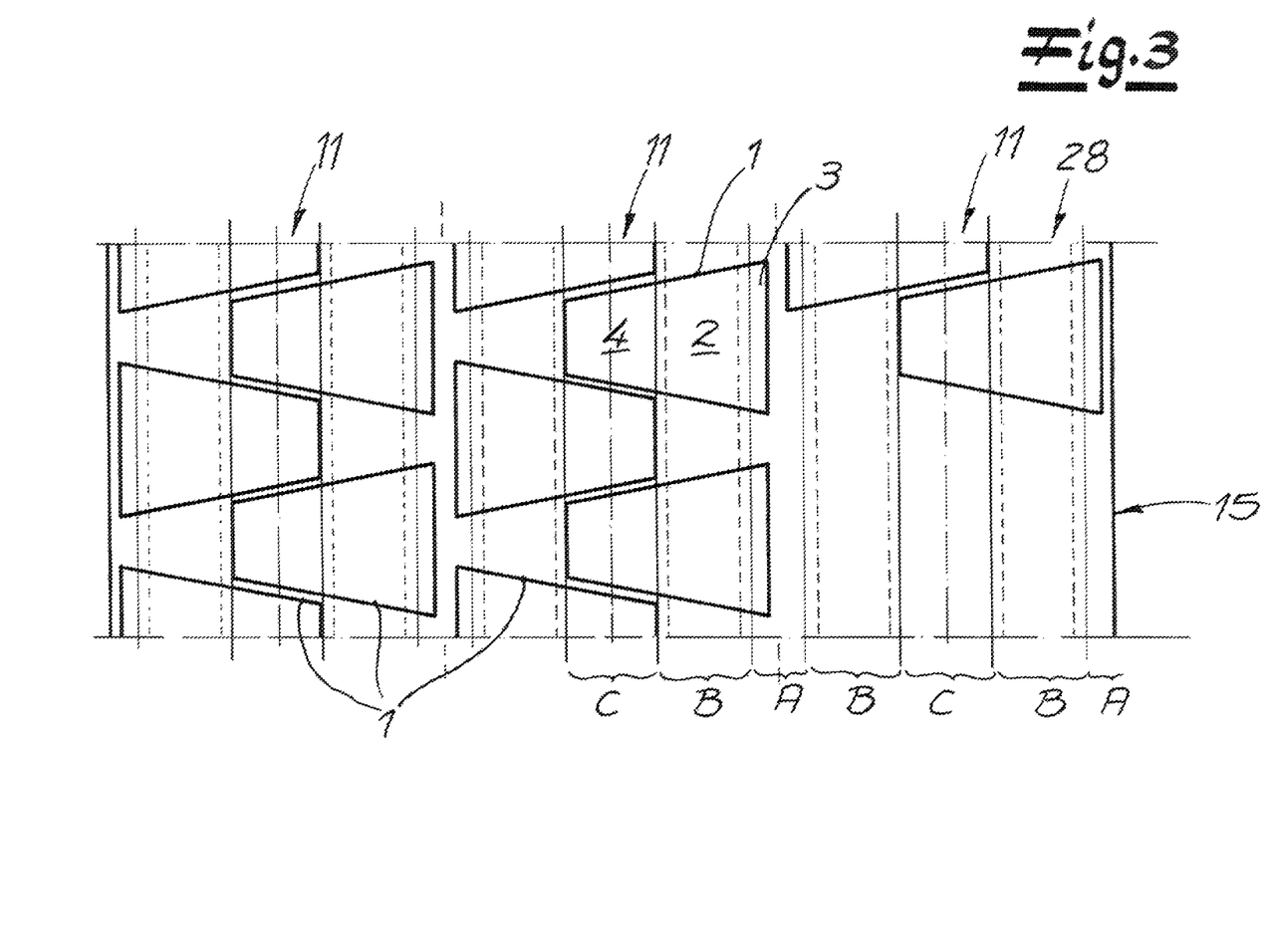
FIG. 3 is a plan view of a web manufactured according to the method of FIG. 2.

FIG. 3 shows a plan view of the laminated multilayer web 15 that has a sequence of three longitudinally extending zones A, B, and C repeating several times, transversely to the moving direction of the web. In a first zone A that corresponds to a region between two strips 28 the nonwoven tapes 12 and 14 are directly bonded to each other. A second zone B that generally corresponds to where the elastic strip 28 is laminated between the overstretched portions of the tapes 12 and 14 is elastically extensible and has outer layers 5 and 6 of nonwoven material as well the strip 28 as core layer 7. The third zone C has outer layers formed by the nonwoven tapes 12 and 14 forming the layers 5 and 6 as well as the strip 11 forming the reinforcing core layer 8. Mechanical activation of the extensible sections creates a tape-like structure when viewed from above, which is dependent upon the profiling of the drawing rollers.

Isosceles-trapezoidal diaper closure elements 1 may be punched from the web 15, with outlines as shown in FIG. 3. The diaper closure elements 1 are each in the shape of so-called diaper ears whose diaper-side connecting region 3, in the travel direction of the web 15, is wider than the respective connecting region 4 for attaching a closure part and falls generally centrally in the zone A. The region 4 for connection to the actual closure element ends in the center of the wide strip 11 forming the reinforced layer 8. The embodiment shows a multiuse web 15 that has several strips 11 of the reinforcing layer.

The tape-like laminated-in reinforcing strips 11 may be applied to the first nonwoven tape 12 in various ways. With the method illustrated in FIG. 2 the reinforcing strips 11 are applied by extrusion coating to the first nonwoven tape 12. The nonwoven tape 12 is passed under a roller 19 whose surface preferably has a structure consisting of elevations and indentations. Application of the polymer is conveniently done by an application tool that pressed down against the nonwoven tape 12 to ensure that the polymer penetrates into the structure of the tape 12. Due to a profiling of the roller surface a polymer pattern with different application amounts can be achieved, and the stiffening effect is influenced.

Advantageous polymer patterns are shown in FIG. 5A to 5H. The directional arrow shown in FIG. 5A to 5H shows the longitudinal extension of a reinforcing layer 8 applied by extrusion coating onto the nonwoven tape 12. The profiling of the roller surface further contributes to an optimal use of the amount of material employed that leads to savings in the material used as stiffening polymer. The application tool may be in the form of coating nozzles arranged in parallel, the distance between the nozzles preferably being adjustable. Alternatively a coating nozzle having a plurality of apertures may be used, with the apertures arranged at a distance adapted to the distance between the reinforcing strips 8. The polymer forming the reinforcing layer 8 can be directly applied to the nonwoven surface.

Figure 4:
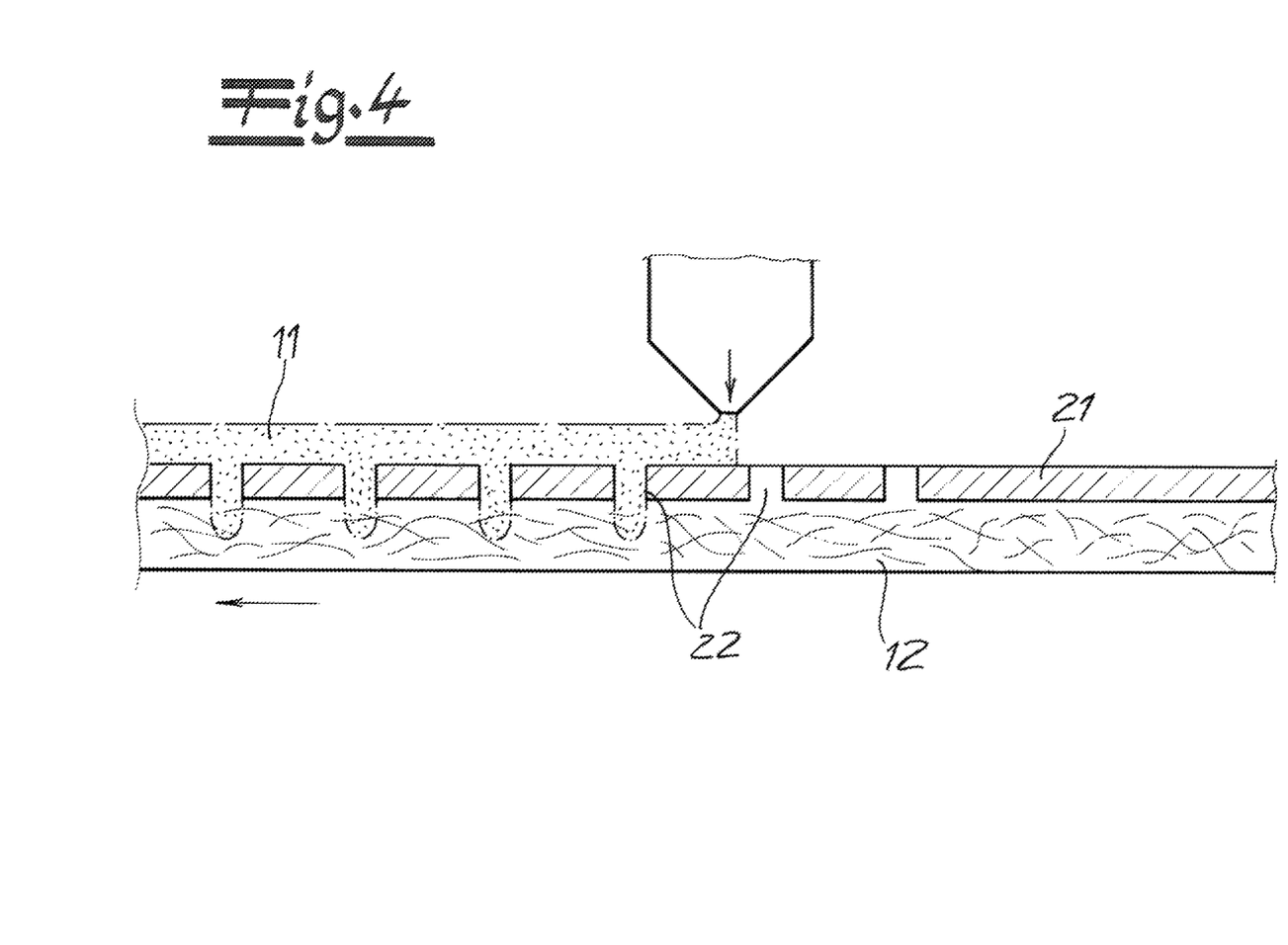
FIG. 4 is a longitudinal section showing how a reinforcing layer is applied to a nonwoven tape by extrusion coating while carrying out the method of FIG. 2.
Figure 5A:
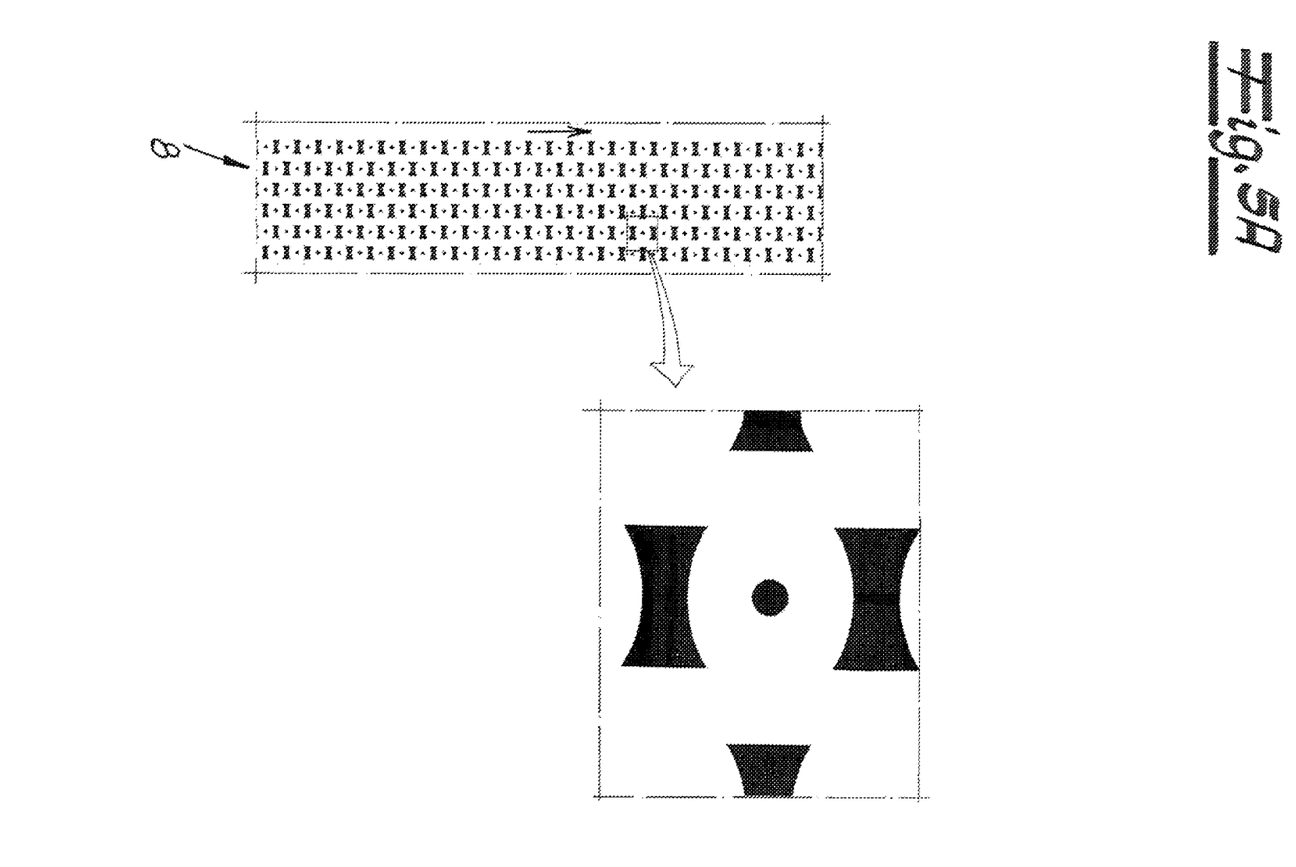
Figure 5B:
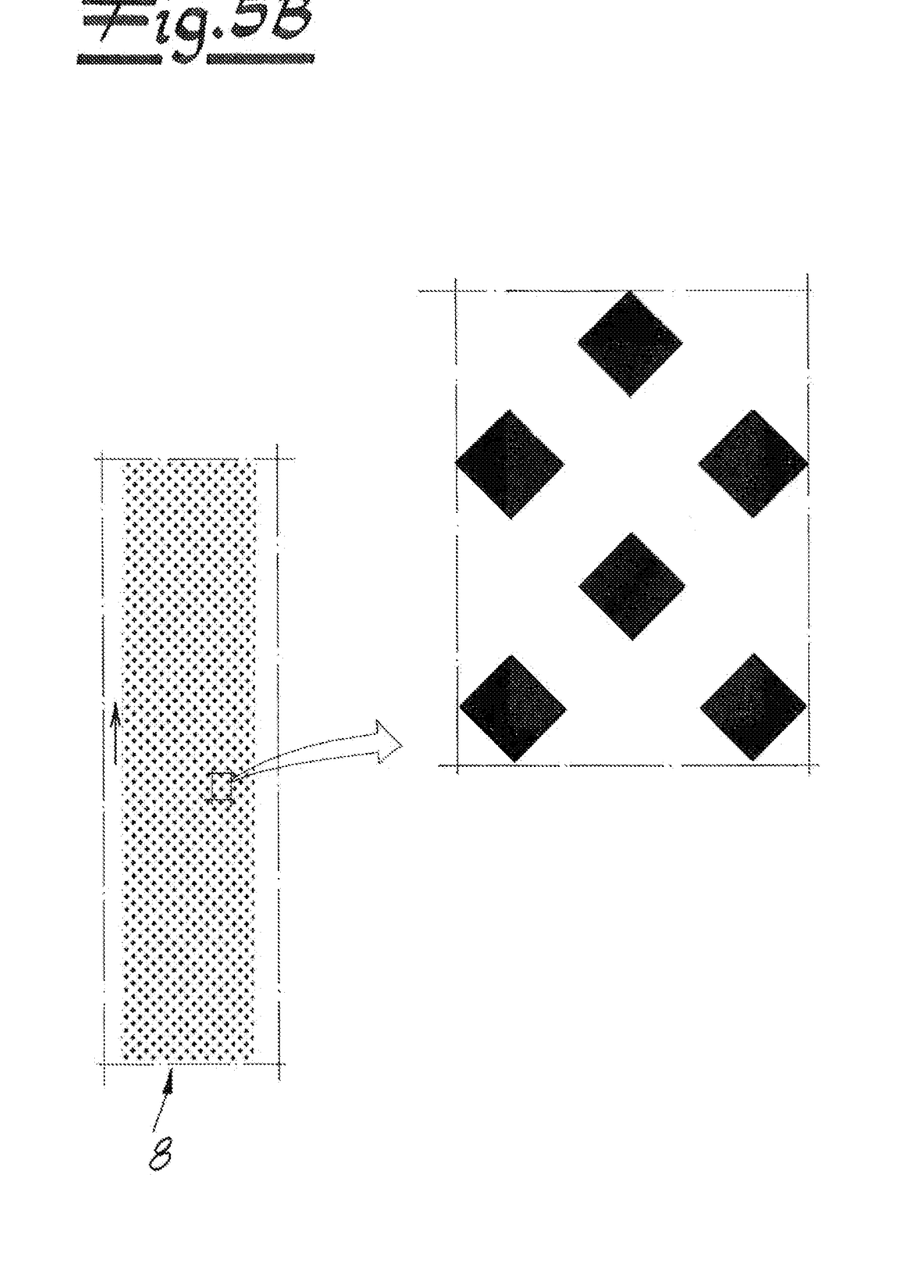
Figure 5C:
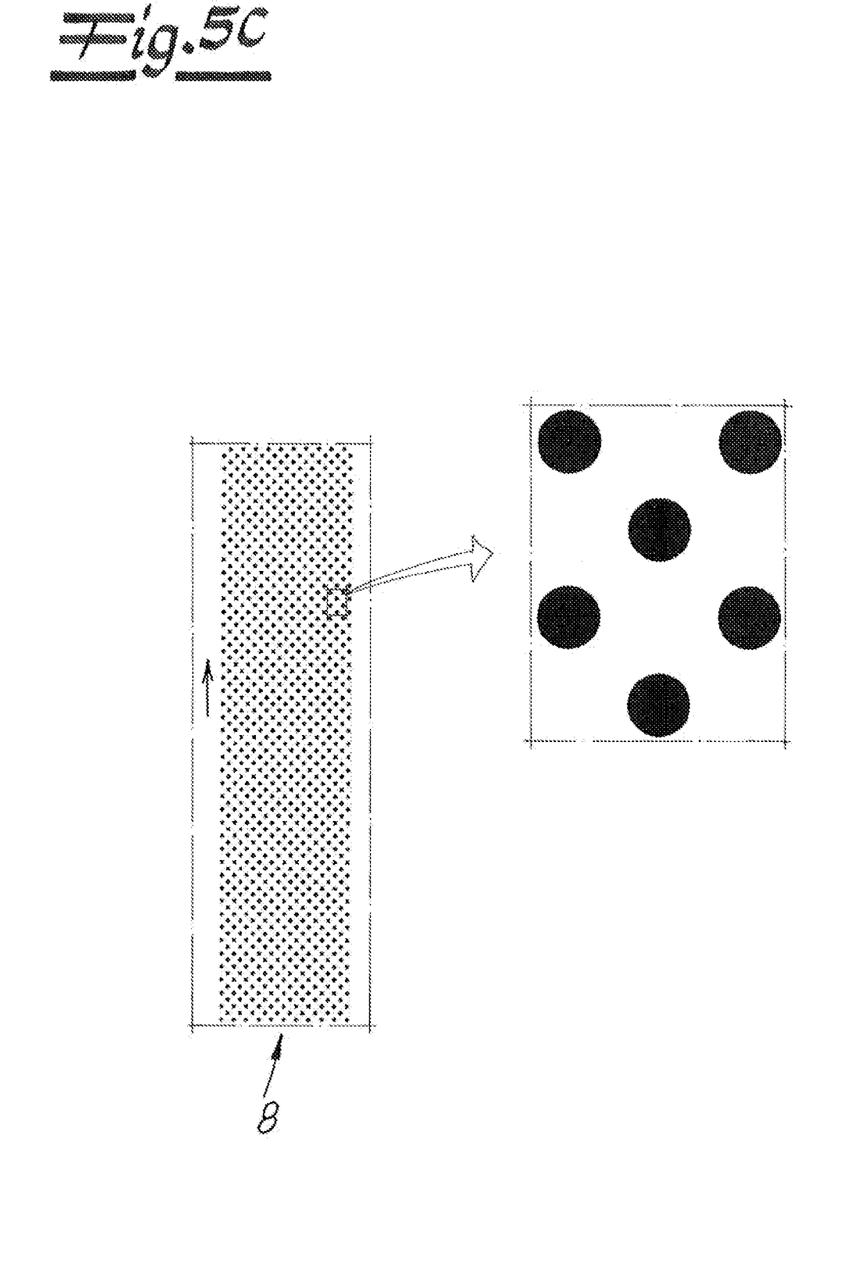
Figure 5D:
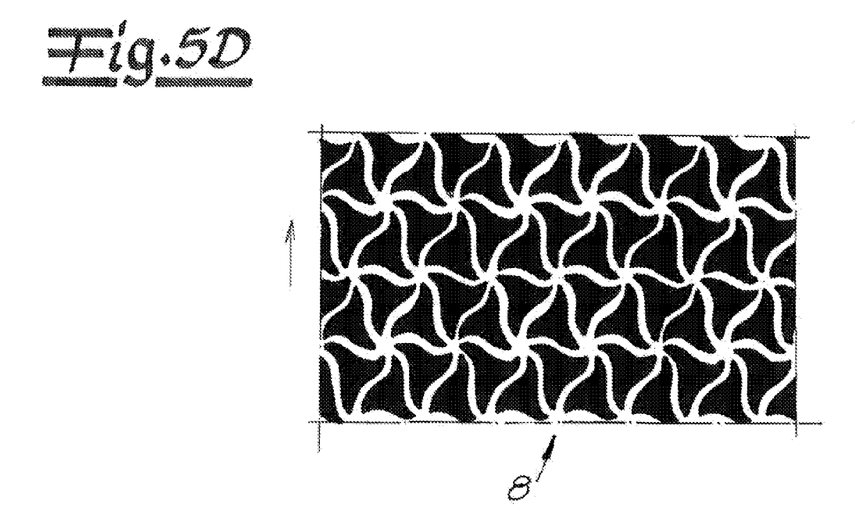
Figure 5E:
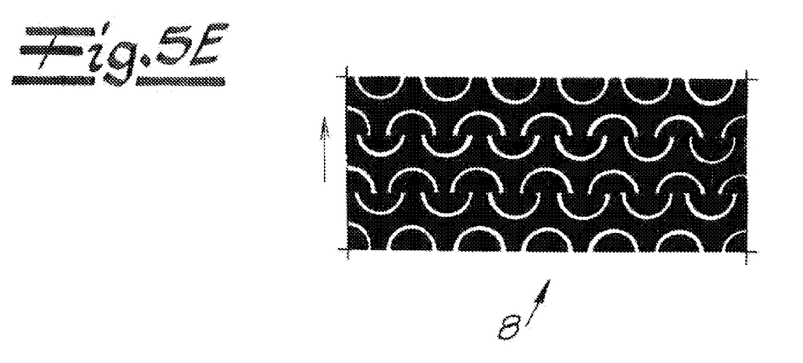
Figure 5F:
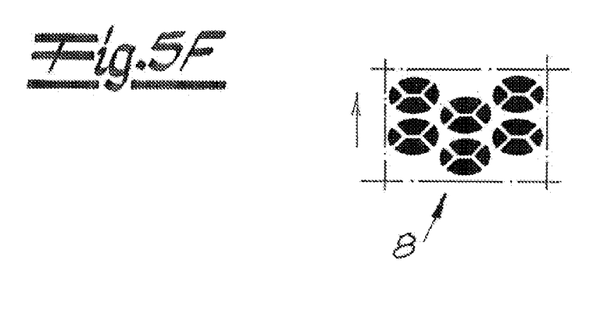
Figure 5G:
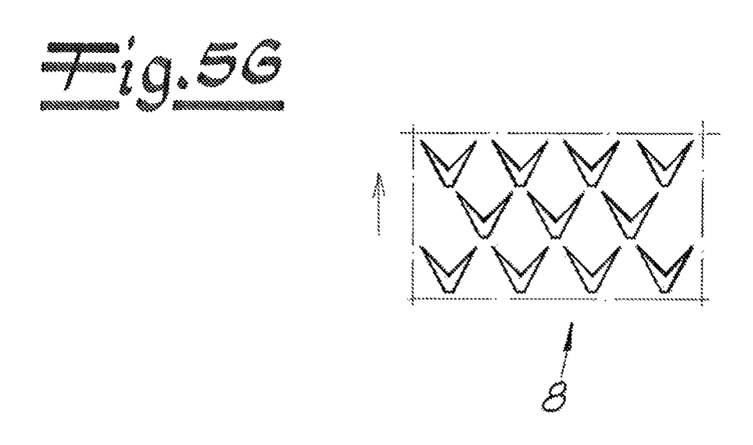
Figure 5H:
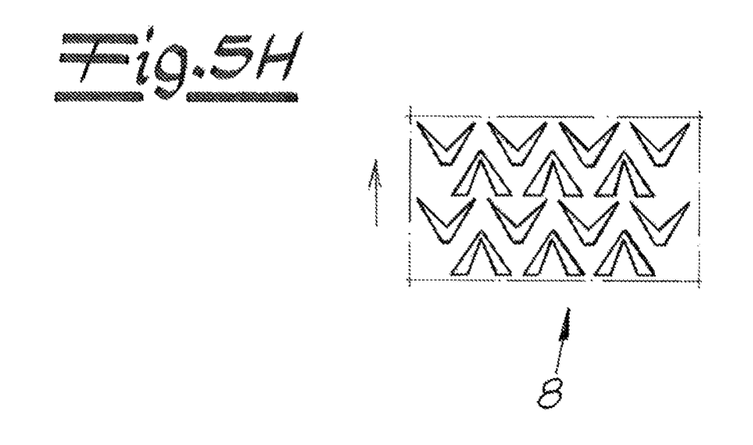

As shown in FIG. 4, according to a preferred embodiment of the method of the invention, however, a stiff perforated film 21 is arranged between the nonwoven tape 12 and the reinforcing polymer forming the strip 11. FIG. 4 shows how a perforated film 21 has been laid onto the nonwoven tape 12 over its entire surface or at least where the reinforcing strip 11 is to be applied. The inelastic polymer for the strip 11 forming the reinforcing layers 8 is applied to the perforated film 21 by extrusion coating such that the molten polymer penetrates through the perforations 22 of the film and bonds with the nonwoven tape 12 at the perforations 22. The film 21 increases the resistance-to-tear propagation. This is due to the fact that the polymer forming the reinforcing strip 11 that, albeit, has good bending resistance properties but mostly only poor tear propagation properties, is no longer bonded full-surface but only in places to the nonwoven tape 12. The polymer compound of the reinforcing layers 8 is thus decoupled from the nonwoven material so that the favorable tear propagation properties of the nonwoven material come into play.

Figure 6:
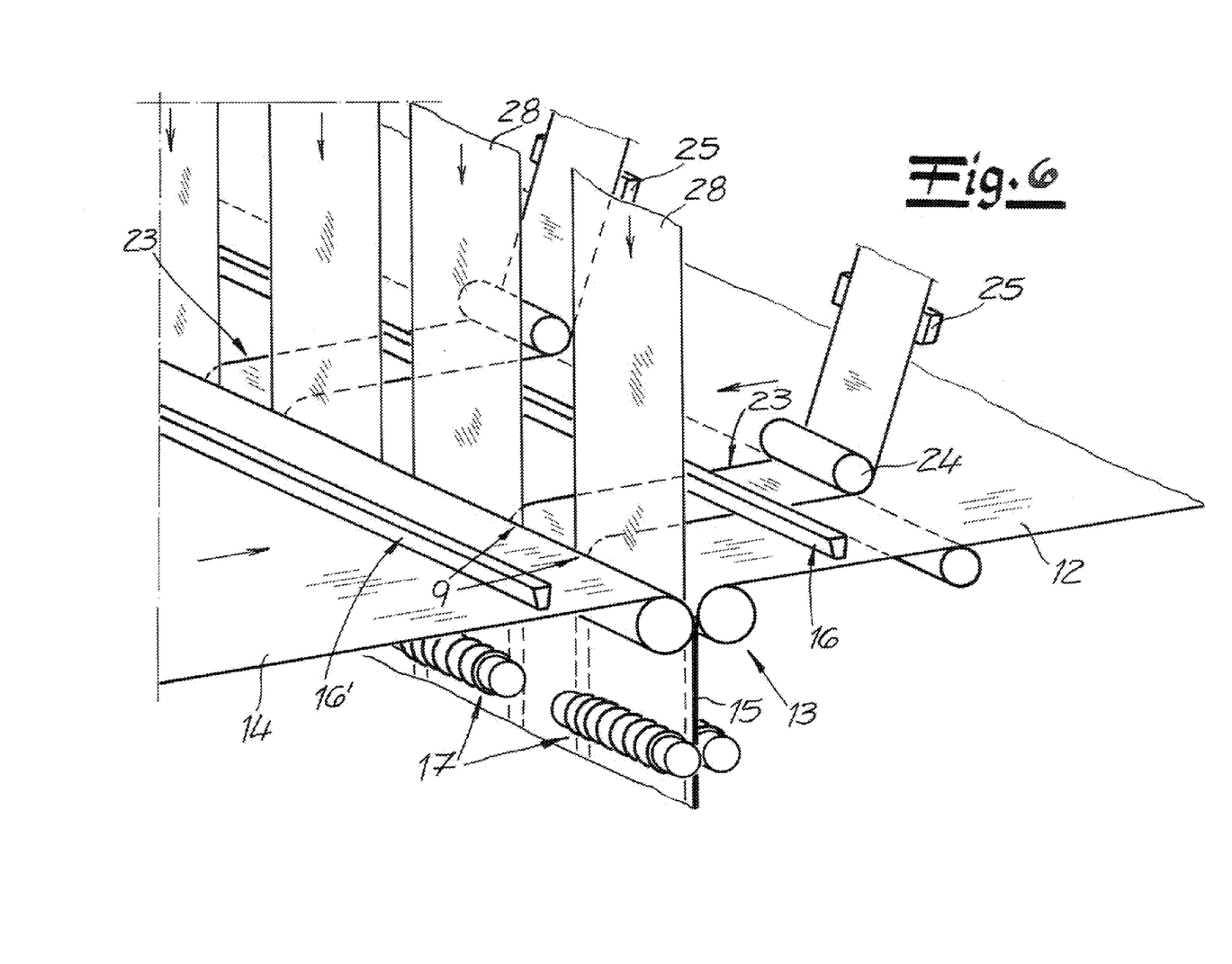
FIG. 6 is a view like FIG. 2 showing another method of making a web from which diaper closure elements as in FIG. 1 may be punched.

With the variant shown in FIG. 6 the manufacture of reinforcing layers 8 involves using reinforcing strips 23 consisting of a bend-resistant polymer film or a nonwoven material. The reinforcing strips 23 are heated by a heater 25 and pressed into the nonwoven tape 12 by embossing rollers 24 using pressure and heat. Alternatively a thermal bond can also be created by ultrasound welding.

Figure 8A:
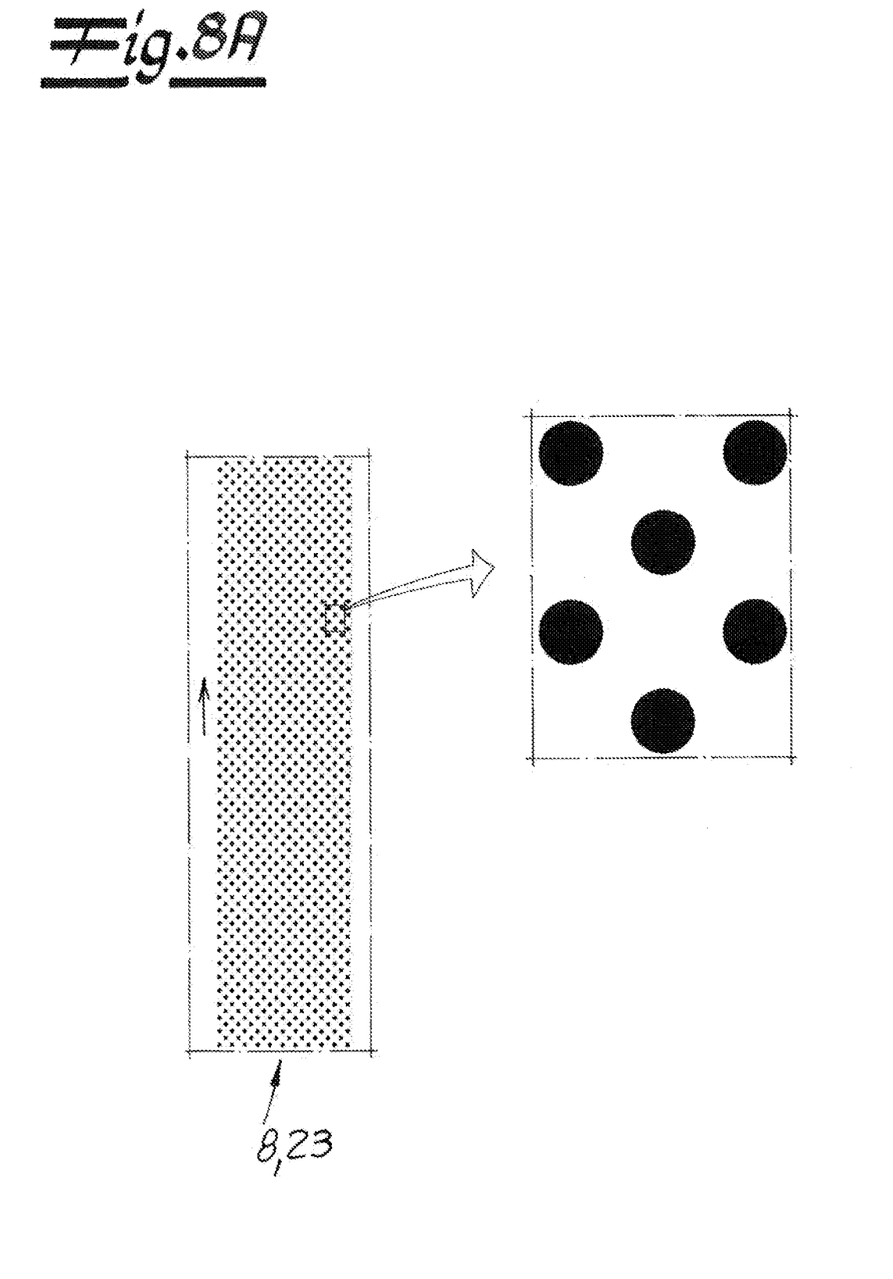
FIGS. 8A to 8C show various patterns for thermal bonding of a reinforcement strip supplied for the FIG. 6 method.
Figure 8B:
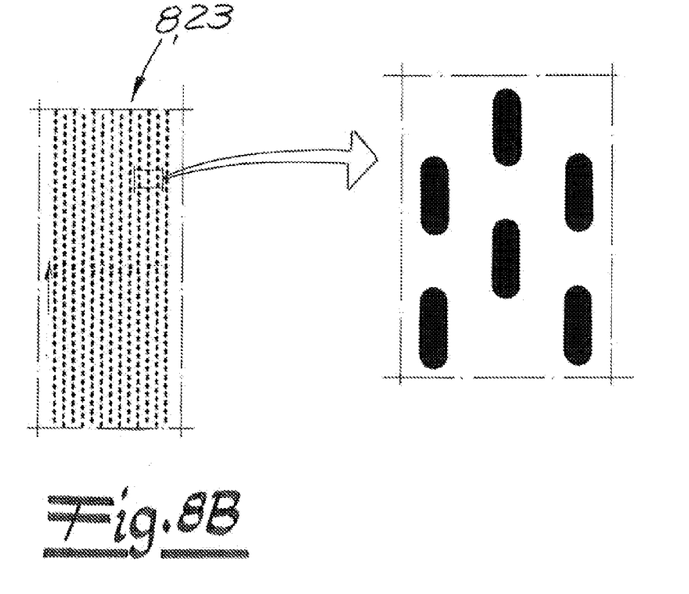
Figure 8C:
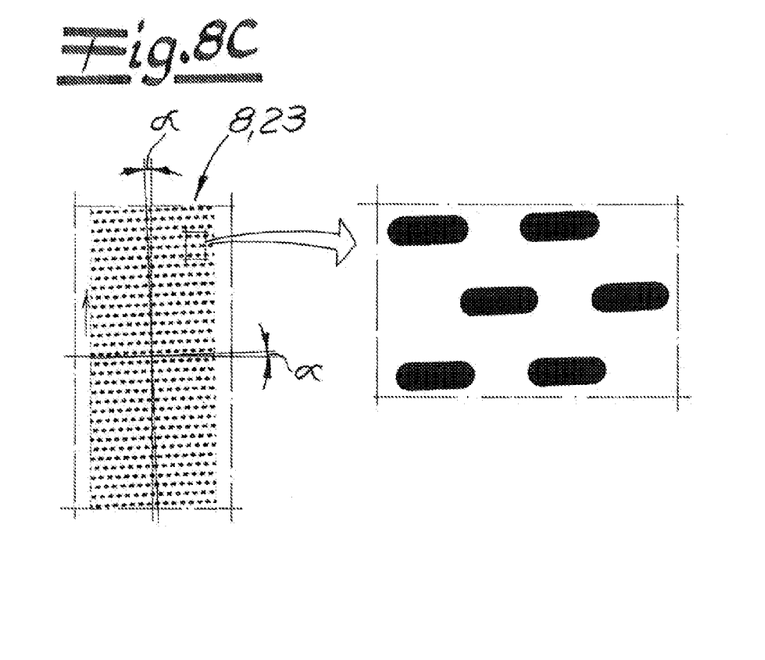

Advantageous patterns that can be created after heating of the reinforcement strips 13 by the embossing roller 24 or alternatively by ultrasound welding, are seen in FIGS. 8A to 10 8C. The directional arrow in FIGS. 8A to 8C shows the longitudinal stretching of the reinforcement strips 23 supplied. The thermal bonding preferably takes place by means of a uniform pattern of bonding locations in the form of points, ellipses or bars, an offset or staggering preferably being provided in the longitudinal direction between successive bonding locations. In the pattern particularly preferred for thermal bonding represented in FIG. 8C, the uniform pattern of bonding locations can be slightly inclined relative to the longitudinal direction, for example by an angle α of 2°.

Figure 7:
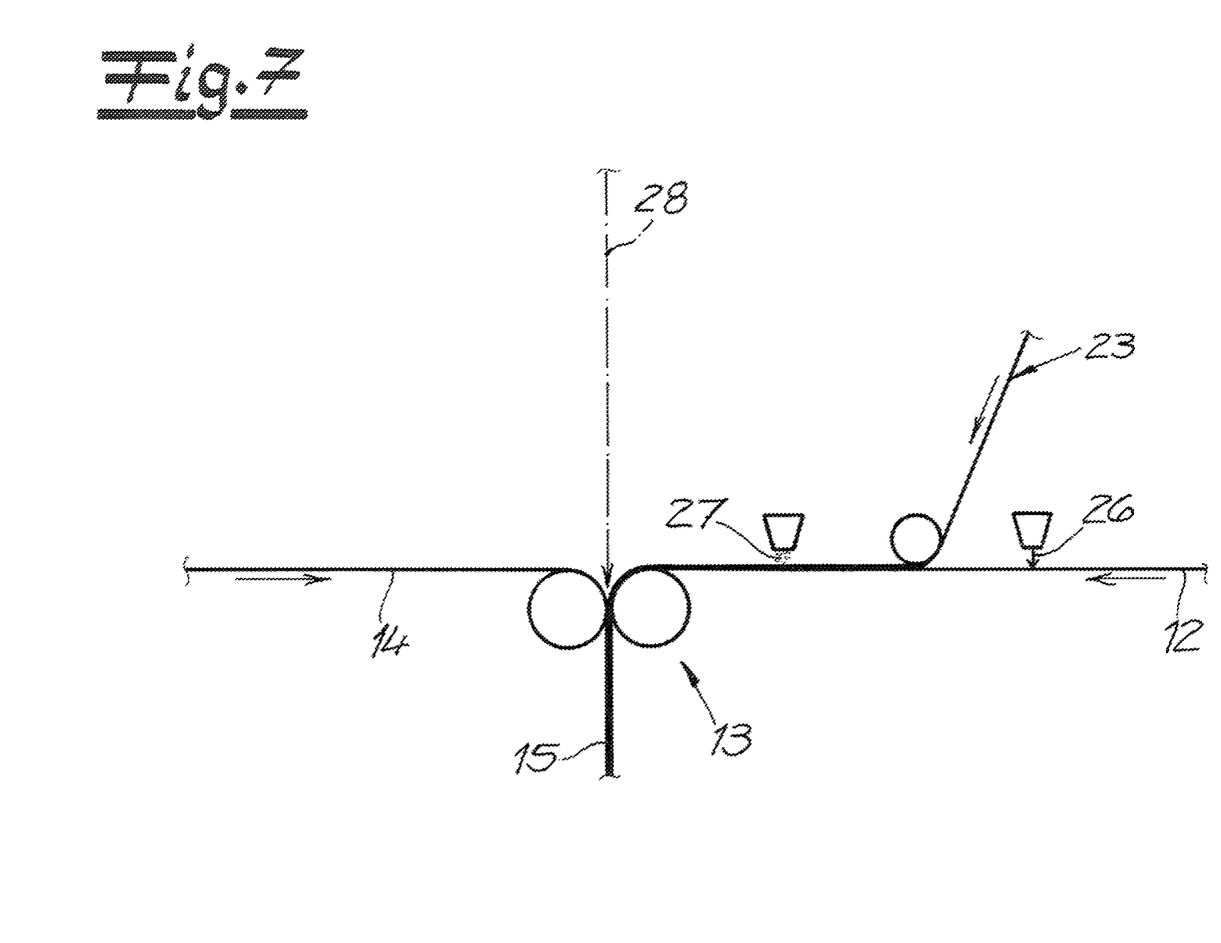
FIG. 7 is a schematic side view illustrating the method of FIG. 6.

With the method also shown in FIG. 7, both faces of the reinforcing strips 23 consisting of a bend-resistant polymer film or a nonwoven material are glued to the nonwoven tapes 12 and 14, the gluing being done such that the glue bonds on the two faces of the reinforcing strips 23 are of different adhesive strength. A selective reduction of adhesive strength on at least one face of the reinforcing strips 23 has a positive effect upon the resistance-to-tear propagation of the laminate. With the method shown in FIG. 7 the reinforcing strips 23, in order to produce different adhesive strengths, are bonded to the respective adjoining nonwoven tapes 12 and 14 by a full coverage with application of adhesive 26 on one face and by partial coverage of adhesive 27 on the other face. For the partial application of adhesive 27 a swirl nozzle technique may preferably be used that enables the adhesive to be distributed across a large region of the surfaces to be bonded. The reinforcing strips 23 may be pretreated by a corona treatment, for example, in order to improve the adhesion of the adhesive

We claim:

1. A method of making diaper closure elements from a laminated web, the method comprising the steps of sequentially:

applying to a first longitudinally extending nonwoven tape at least two pairs of longitudinally extending and transversely spaced strips of an elastically stretchable polymer;

applying to the first nonwoven tape only between each of the pairs of the stretchable polymer strips a respective longitudinally extending bend-resistant strip with the bend-resistant strip partially overlapping both of the polymer strips of the respective pair;

applying over the bend-resistant strips and the stretchable polymer strips a second longitudinally extending nonwoven tape to form a laminate with the stretchable polymer strip between the first and second nonwoven tapes; and punching the closure elements from the web with one end of each element lying between the bend-resistant strips of a respective one of the pairs of elastically stretchable polymer strips and an end of each element opposite the respective one end lying between the respective one pair of polymer strips and an adjacent pair of elastically stretchable polymer strips.

2. The method defined in claim 1, further comprising the step of hot bonding the stiff strips to the first nonwoven tape.

3. The method defined in claim 1 wherein a hot-melt adhesive is used to secure the stiff strips to the first nonwoven tape.

4. The method defined in claim 1 wherein the stiff strips are hot bonded to the first nonwoven tape by hot embossing rollers.

5. The method defined in claim 1 wherein the stiff strips are adhesively bonded to the first nonwoven tape.

6. The method defined in claim 1 wherein the bend-resistant strips are of polyolefins, polyolefin copolymers, styrene polymers, cycloolefin copolymers, polyamides, a polyactide, polyester, thermoplastic polyurethanes or mixtures of these polymers.

7. The method defined in claim 1, further comprising the step of stretching the laminate substantially only at the polymer strips transversely thereof so as to overstretch the first and second nonwoven tapes thereat.

8. The method defined in claim 1, further comprising the step of:

leaving longitudinally extending spaces between adjacent pairs of the stretchable polymer strips free such that the first and second nonwoven tapes directly engage each other between adjacent pairs of the stretchable polymer strips.

9. A method of making diaper closure elements from a laminated web, the method comprising the steps of sequentially:

applying to a first longitudinally extending nonwoven tape at least two pairs of longitudinally extending and transversely spaced strips of an elastically stretchable polymer;

applying to the first nonwoven tape between each of the pairs of the stretchable polymer strips a respective longitudinally extending stiff polymer or nonwoven bend-resistant strip with the bend-resistant strips partially overlapping both of the polymer strips of the respective pair;

applying over the bend-resistant strips and the stretchable polymer strips a second longitudinally extending nonwoven tape to form a laminate with the stretchable polymer strip between the first and second nonwoven tapes; and punching the closure elements from the web with one end of each element lying between the bend-resistant strips of a respective one of the pairs of elastically stretchable polymer strips and an end of each element opposite the respective one end lying between the respective one pair of polymer strips and an adjacent pair of elastically stretchable polymer strips.

10. The method defined in claim 9 wherein the first nonwoven tape is secured by a relatively strong bond to the stiff strips and to the polymer strips and the second nonwoven tape is secured by a less strong bond to the stiff strips and polymer strips.

11. The method defined in claim 9 wherein the stiff strips are pretreated on both faces to improve bonding.

12. The method defined in claim 9 wherein the stiff strips are each pretreated on only one face for differential bonding to the first and second nonwoven tapes.

13. A method of making a laminated web from which diaper closure elements may be punched, the method comprising the steps of sequentially:

securing a first longitudinally extending nonwoven tape with a relatively strong bond to at least two pairs of longitudinally extending and transversely spaced strips of an elastically stretchable polymer;

securing to the first nonwoven tape between each of the pairs of the polymer strips by another relatively strong bond a respective longitudinally extending stiff polymer or nonwoven bend-resistant strip with the bend-resistant strips partially overlapping both of the polymer strips of the respective pair; and securing over the bend-resistant strips and the polymer strips by a less strong bond a second longitudinally extending nonwoven tape to form a laminate with the polymer strip between the first and second nonwoven tapes.

14. The method defined in claim 13 wherein the relatively strong bond is a full-coverage bond and the less strong bond is a partial-coverage bond.

15. The method defined in claim 14 wherein the partial-coverage bond is made by a swirl nozzle.

* * * * *